United States Patent [19]

Wagner et al.

[11] Patent Number: 4,720,456
[45] Date of Patent: Jan. 19, 1988

[54] TREHALOSE LIPID TETRAESTERS

[75] Inventors: Fritz Wagner, Stockheim; Egbert Ristau, Wolfsburg; Zu-yi Li; Siegmund Lang, both of Brunswick; Walther Schulz, Staufenberg; Hans-Jurgen Hofmann, Vechta; Kai-Udo Sewe, Barnstorf; Walter Lindorfer, Kassel, all of Fed. Rep. of Germany

[73] Assignee: Wintershall AG, Kassel, Fed. Rep. of Germany

[21] Appl. No.: 898,838

[22] Filed: Aug. 20, 1986

Related U.S. Application Data

[63] Continuation of Ser. No. 609,120, May 11, 1984, abandoned.

[51] Int. Cl.$^4$ .................. C12P 19/44; C12N 1/28; C07G 11/00
[52] U.S. Cl. .................................... 435/74; 435/249; 536/16.8
[58] Field of Search ................. 536/16.8; 435/74, 249

[56] References Cited

FOREIGN PATENT DOCUMENTS 3248167 6/1984 Fed. Rep. of Germany ...... 435/249

OTHER PUBLICATIONS

Biotechnology Letters, vol. 5, No. 2, pp. 95–100, (1983); Ristau et al.
Chemical Abstracts, vol. 98, (1983), #122523s, Ristau et al.
Chemical Abstracts, vol. 85, (1976), #44944v, Suzuki et al.
Chemical Abstracts, vol. 95, (1981), #162914q, Kilburn et al.

Primary Examiner—Jerome D. Goldberg
Assistant Examiner—Joseph A. Lipovsky
Attorney, Agent, or Firm—Michael N. Meller

[57] ABSTRACT

Anionic, surface-active trehalose lipids, in which different organic acids are bound to a trehalose molecule by an ester linkage, are prepared by aerobically cultivating trehalose-producing microorganisms, capable of assimilating hydrocarbons, under growth-limiting conditions, but without limiting the oxygen.

6 Claims, No Drawings

TREHALOSE LIPID TETRAESTERS

This application is a continuation of application Ser. No. 609,120, filed May 11, 1984, now abandoned.

BACKGROUND OF THE INVENTION

Trehalose lipids are known glycolipids, which contain trehalose as the disaccharide moiety and exhibit surface-active properties. The trehalose lipids can be prepared by means of microorganisms, for example as is known from U.S. Pat. No. 4,286,660. According to this method, an aqueous nutrient solution is mixed in a bioreactor with n-alkanes having a $C_8$ to $C_{24}$ chain length or with crude oil and this mixture is inoculated with a microorganism. The growth is carried out with an aeration rate of 0.5 to 1.0 V/V/min and an agitation speed of 400 to 1200 rpm at a temperature of 30° C. to 50° C., wherein the pH of the liquid culture is maintained at 6.8 to 7.0 by the addition of aqueous ammonia. The growth is terminated by a temperature shock, i.e. short heating of the liquid culture at a temperature of 60° C. The cell mass is separated from the culture suspension. The remaining aqueous phase can be used directly or can be worked up to isolate glycolipids by known methods, for example, by extraction with a suitable solvent which is evaporated from the extract after separation from the culture solution.

According to this known process, trehalose lipids of the general formulae given below are obtained using the microorganisms *Nocardia rhodochrous* or *Mycobacterium phlei*.

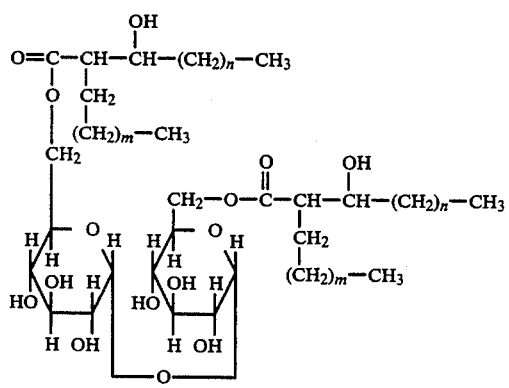

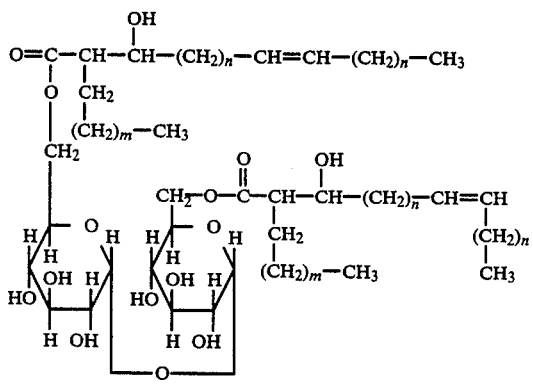

The yields of the trehalose lipids from this process lie between 600 and 700 mg/l of aqueous phase isolated from the liquid culture.

Hitherto only those trehalose lipids have been regarded as non-ionic surface-active substances which are esterified by a fatty acid in the $CH_2OH$ groups in the $C_6$ position, so that the corresponding trehalose lipids have been called trehalose diesters.

These known trehalose lipids can be represented by the general formula

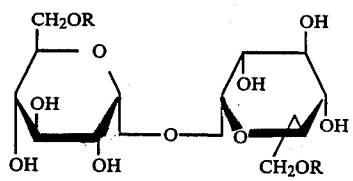

wherein $R_1$ and $R_2$ can be the following radicals:

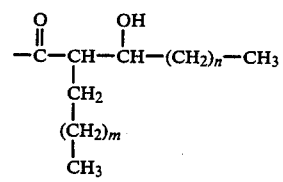

with m=8 to 10 and n=18 to 21 or

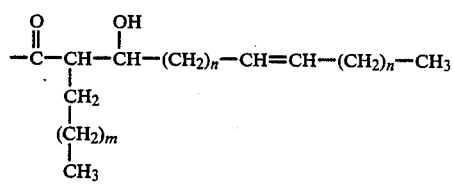

with m=20 to 22 and n=14 to 17.

These compounds, which are non-ionic surface-active substances, can be considered as diesters of trehalose. They were obtained by this process in yields of 600 to 700 mg/l of the nutrient solution.

In a publication by S. G. Batrakov et al in "Chemistry and Physics of Lipids", 29 (1981), pages 241 to 266, a new type of trehalose lipids was reported which can be isolated from the cell mass of the paraffin oxidizing bacterium *Mycobacterium paraffinicum*. In addition to the known di-fatty acid esters of trehalose, such as 6,6'-di-O-mycolyl-α,α-D-trehalose, 6-0-mycolyl-α,α-D-trehalose and 6,6'-di-0-acyl ($C_{12}$–$C_{16}$)-α,α-D-trehalose, the compounds 6-0-mycolyl-6'-0-acyl ($C_{12}$–$C_{16}$)-α,α-D-trehalose and 2octanyl-3,2'-di-0-decanoyl-6-0-succinoyl-α,α-D-trehalose were isolated and identified.

According to J. F. T. Spencer et al in "Canadian Journal of Chemistry" 39 (1961), page 846, the fermentation of *Torulopsis bombicola* produces sophorolipids of the general formula:

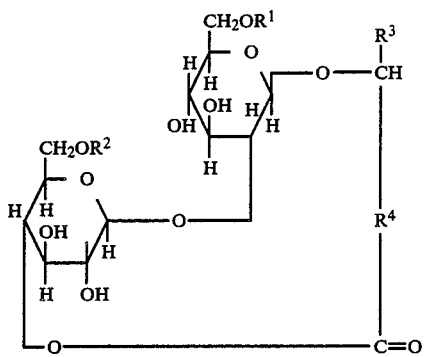

in which $R^1$ and $R^2$ are H or

group, $R^3$ is H or a —CH₃ group and $R^4$ is a saturated or unsaturated $C_{11}$–$C_{16}$ hydrocarbon radical. These sophorolipids are obtained in the lactone form as shown in equilibrium with free acids formed by hydrolysis of the lactone bond. These sophorolipids are thus partly diacetyl esters.

According to U.S. Pat. No. 4,276,377, a glycolipid. methyl ester with surface-active and waxy properties can be obtained if a hydrated sophorolipid obtained by fermentation of *Torulopsis bombicola* is mixed with certain ether-alcohols and water is distilled off from this mixture. Whereupon, the anhydrous system of sophorolipids and ether-alcohol will undergo a methanolysis and a methylation reaction with methanol in the presence of a strong acid. Thereby both acetyl groups are split off and the acid groups esterified with methanol. This ester no longer has any ester groups in the sophorose part of its molecule, but only a lower alkyl ester of a carboxylic acid group of the fatty acid forming the lipid part of the molecule. Since the hydroxyl groups of the sophorose part of this ester are free, this non-ionic surfactant exhibits a high surface activity, which can be modified by ester exchange of the alcoholic methyl ester group with other alcohols having longer carbon chains in the molecule.

SUMMARY OF THE INVENTION

The object of the invention is to increase the yield of glycolipids, especially trehalose lipids, in biological processes and, if necessary, to find simple means by which glycolipids, especially trehalose tetraesters, can be obtained.

Trehalose lipids have been found in which different organic acids are esterified with a trehalose molecule according to the general formula

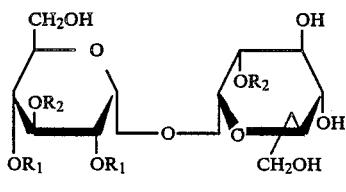

where

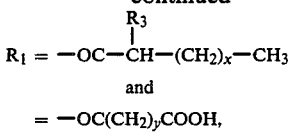

as well as

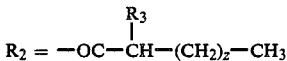

in which
x=4 to 22
y=1 to 4
z=4 to 22
$R_3$=H or an alkyl group.

These trehalose lipids are anionic surface-active substances, which have a higher surface activity than the non-ionic surface-active trehalose lipids.

DETAILED DESCRIPTION

The preparation of the trehalose lipids of the invention is carried out by cultivating trehalose lipid-producing and alkane-utilizing microorganisms in a hydrocarbon-containing aqueous culture medium with a certain pH at a temperature below 50° C. and final isolation of the trehalose lipids from the culture suspension. According to the invention, the microorganisms are cultivated aerobically at a pH of 3 to 8 and a temperature of 15 to 50° C. with limitation of the growth rate.

The production of the desired trehalose lipids can be attained by stirring into the culture suspension, at intervals during the period of logarithmic growth, several portions of an organic solvent which is not miscible with water, preferably a hydrocarbon solvent, in amounts which will not interfere with the growth of the microorganism. Preferred examples of solvents for this purpose are kerosene and n-paraffin S. The kerosene contains 85 vol. % of saturated hydrocarbons and about 15 vol. % of aromatic hydrocarbons and the n-paraffin S contains about 89 vol. % of $C_{14}$ hydrocarbons and about 9 vol. % of $C_{15}$ hydrocarbons An aqueous nutrient salt solution, which supplies the total growth needs of the trehalose lipid-producing microorganism, is the basis of the culture medium. After sterilization of the culture medium, sterile, assimilable hydrocarbons, especially n-Paraffin S, are added thereto. After adjusting the pH of the liquid culture medium to a value between 3 and 8 with an aqueous solution of an alkaline compound, e.g. an ammonia solution, this culture solution is inoculated with a submerged culture of the trehalose lipid-producing microorganism. The obtained culture suspension is aerated at the initial pH and a temperature of 15 to 50° C. with air enriched with 40 vol. % oxygen at a rate of 0.5 V/V/m with stirring at 1500 rpm. During the logarithmic growth phase, several portions of an organic solvent, which is not miscible with water, preferably containing hydrocarbons, can be stirred into the culture suspension at intervals. Using kerosene as the substrate and solvent, it has proven advantageous to add, after an initial growth period of 14 hours, 10 g/l of kerosene; after another 11 hours, 16 g/l; after another 5 hours, 18 g/l; and after another 10 hours, 10 g/l. The growth of the microorganism is not arrested by addition of these amounts of kerosene. The kerosene rather clearly increases the permeability of the lipophilic cell walls and dissolves the trehalose lipids clinging to the cell walls, whereby the microorganism is obviously stimulated to produce further amounts of trehalose lipids, since the yields of trehalose lipids of 776 to 800 mg/l according to this embodiment of the process clearly exceed the yields of 600 to 720 mg/l of culture suspension according to the known process of U.S. Pat. No. 4,286,660.

In the same way, n-Paraffin S can be added as the substrate and organic solvent according to the process of the invention. Accordingly, it has been found advantageous to add 20 g/l of n-Paraffin S to the culture suspension after an initial growth period of 17 hours. Additional amounts of 12 g/l were added to the suspension after another 32 hours and another 10 hours. According to this embodiment of the process of the invention, the yields of trehalose lipids exceeded 2,000 mg/l.

Another way to limit the process of the invention is to stir into the culture suspension, depending on the growth of the trehalose lipid-producing microorganism, a complex-former for polyvalent inorganic cations, preferably ethylenediaminetetraacetic acid, which decreases, but does not stop, the growth of the microorganism. It has proven advantageous to combine the addition of the ethylenediaminetetraacetic acid, preferably as the disodium salt, with the addition of the aqueous solution of an alkaline compound, e.g. ammonia, for adjusting the pH of the culture suspension so that the ethylenediaminetetraacetic acid is incorporated into this aqueous solution in suitable amounts. Preferably, at least 46 to 47 g/l of ethylenediaminetetraacetic acid, or a corresponding amount of the disodium salt of this acid, are dissolved in a solution containing 10% by volume of ammonia. In this way, about 3.75 g/l of the disodium salt of ethylenediaminetetraacetic acid are added to the culture suspension during the growth period. The yields of trehalose lipids according to this embodiment of the process of the invention amount to about 3,250 g/l.

The standard rule applies that at least one mole of ethylenediaminetetraacetic acid is added per mole of divalent cations and per mole of trivalent cations dissolved in the culture suspension. By the addition of ethylenediaminetetraacetic acid, the polyvalent cations increasingly present dissolved in the culture suspension during the growth period, are held in a complex and thus are only available in limited concentration as nutrients for the microorganism.

A further possibility for increasing the yield of trehalose lipids according to the invention consists in limiting the source of nitrogen in the culture suspension, which reaches a suitable predetermined level and is maintained thereat, by adding a nitrogen-free alkaline compound, such as an alkali metal hydroxide, to maintain the pH value of the culture suspension at the selected value. In this way, the nitrogen content of the culture suspension is limited to the amount which is dissolved in the initially added nutrient salt solution. The yields of trehalose lipids from this embodiment of the invention amount to about 5,000 mg/l of culture suspension.

In addition to the above described limiting features, the temperature of the culture suspension can also be raised or lowered to 15° C. at the end of the logarithmic growth period. For example, by simultaneous limitation of the nitrogen, according to this variant of the process of the invention, over 7,800 mg of trehalose lipids are obtained per 1 of culture suspension.

A further increase in the yield of trehalose lipids can be obtained, according to the inventron, by adding a bacteriostatic agent, e.g., at least 0.01 to 0.02 g/l of d-N,N'-bis(1-hydroxymethylpropyl)ethylenediamine dihydrochloride (Ethambutol) to the nutrient salt solution after its sterilization. With simultaneous nitrogen limitation and temperature lowering during the growth period, the yield of trehalose lipids rises to over 10,000 mg/l of culture suspension, according to this variant of the process of the invention.

The isolation of the trehalose lipids, obtained according to the different embodiments of the process according to the invention, is accomplished by known methods. Thus, the culture solution can be exhaustively extracted with a mixture of methylene chloride/methanol in the volume ratio of 2:1. The obtained extract is then concentrated under vacuum to yield a crude extract, from which the unreacted hydrocarbons are separated. These can then be reused in the process of the invention. The residue comprises a mixture of trehalose lipids which contains, depending upon the particular embodiment, up to 10 to 40 wt. % of non-ionic and up to 60 to 90 wt. % of anionic trehalose lipids comprising 0.75 to 10.5 g/l of the culture suspension.

The separation of this mixture into its components can be carried out by known methods, as, for example, in Example 10.

*Rhodococcus erythropolis* DSM 43 215 as well as *Arthrobacter* spec. DSM 2567 and *Corynebacterium* spec. DSM 2568 are preferably used as the trehalose lipid-producing microorganisms.

The invention makes it possible to increase the yield of trehalose lipids obtained by biotechnological means to a surprising degree and, at the same time, to obtain previously unknown anionic surface-active trehalose lipid tetraesters, whereby the chain length of the acid portion of these esters varies according to the nature of the substrate. By suitable choice of the variables of the process of the invention, it is further possible to change the composition of the trehalose lipids of the invention and to influence the surface activity of these products, since the new anionic trehalose lipids are more hydrophilic than the non-ionic trehalose lipids. The surface activity of the products of the invention can be further influenced by making chemical derivatives, such as for example, by esterification.

EXAMPLE 1

Gradual Addition of Kerosene

A 100 l bioreactor, provided with an intensor system was charged with 50 l of a nutrient salt solution (comprising 500 g yeast extract, 62 g citric acid $\times 1H_2O$, 100 g $(NH_4)_2SO_4$, 25 g $KH_2PO_4$, 25 g $Na_2HPO_4 \times 2H_2O$, 50 g 85% $H_3PO_4$, 2.5 g $CaCl_2 \times 2H_2O$, 1 g $FeCl_3 \times 6H_2O$, 10 g $FeSO_4 \times 7H_2O$, 55 g $MgSO_4 \times 7H_2O$ and 50 l tap water), and sterilized at pH 3.0 and a temperature of 121° C. for 30 min. After cooling to 30° C., 2,200 g sterile Paraffin S (89% C-14, 9% C-15), were added and the pH adjusted to 5.8 with 5% $NH_4OH$ solution. The mixture was then inoculated with 5,000 ml of a 24 hr.-old submerged culture of *Rhodococcus erythopolis* DSM 43 215. During the growth period, the submerged culture was automatically maintained with a pH controller at a constant pH of 5.8 by titration with 5 vol. % ammonia solution and was aerated at a temperature of 30° C. at agitation speed of 1500 rpm and an aeration rate of 0.5 V/V/m of 40 vol. % oxygen-enriched air. After a cultivation period of 14 hrs., 500 g of kerosene was added, followed by 800 g after 25 hrs., 900 g after 30 hrs. and 500 g after 40 hrs. The composition of the kerosene was 85 vol. % saturated hydrocarbons and 15% aromatic hydrocarbons. The cultivation was ended after 50 hrs. after which the obtained submerged culture (containing 1,150 g of dry cell weight) was exhaustively extracted in known manner with methylene chloride/methanol (2:1 vol/vol). The combined organic extract was concentrated under vacuum. The residue (2700 g) was taken up in 10 l chloroform, treated with 5,000 g silica gel 60 and the obtained suspension filtered. The filtrate, after concentration under vacuum, contained 2,650 g hydrocarbons, which were recycled. The glycolipids absorbed on the silica gel were exhaustively extracted with $CH_3OH$ and the purified $CH_3OH$ extract concentrated under vacuum. The residue contained 20.2 g of trehalose mycolate or 40% calculated on the total trehalose lipids and 18.6 g of trehalose tetraester or 60% based on the total trehalose lipids.

EXAMPLE 2

Gradual Addition of n-Paraffin S

*Rhodococcus erythropolis* DSM 43 215 was cultivated as in Example 1, except that, instead of the kerosene, 1,000 g of n-Paraffin S (composition: 89% C-14, 9% C-15) were added after 17 hrs., 600 g after 49 hrs. and 600 g after 59 hrs. The cultivation was ended after 64 hrs. The extraction was carried out as in Example 1. The crude organic extract contained, in addition to n-Paraffin S (450 g) which was recycled, 31.65 g of trehalose mycolate or 20%, based on the total trehalose lipids, and 77.86 g of trehalose tetraester or 80%, based on the total trehalose lipids.

EXAMPLE 3

Limitation of polyvalent cations by continuous addition of ethylenediaminetetraacetic acid A 100 l bioreactor, provided with an intensor system, was charged with 50 l of a nutrient salt solution (composition: 50 g yeast extract, 121 g citric acid $\times 1H_2O$, 23.5 g $(NH_4)_2SO_4$, 184 g $KH_2PO_4$, 71.5 g $Na_2HPO_4 \times 2H_2O$ 50 g 85% $H_3PO_4$, 21.5 g $CaCl_2 \times 2H_2O$, 12.5 g $FeCl_3 \times 6H_2O$, 76.5 g $MgSO_4 \times 7H_2O$, 2 g Kcl and 50 l tap water), sterilized at pH 3.0 and a temperature of 121° C. After cooling to a temperature of 30° C., the reactor was charged with 4,900 g of sterile n-Paraffin S (89% C-14, 9% C-15), the pH adjusted to 5.8 with 5% $NH_4OH$ solution and the mixture was inoculated with 5,000 ml of a 24-hr.-old submerged culture of *Rhodococcus erythropolis* DSM 43 215. During the cultivation, the submerged culture was automatically maintained with a pH controller at a constant pH of 5.8 by titration with 10 vol. % ammonia solution which contained 46.74 g ethylenediaminetetraacetic acid per liter. The culture was aerated at a temperature of 30° C., a stirring rate of 2,000 rpm and an aeration rate of 1.5 V/V/m with air at a constant reactor pressure of 2 bars. Altogether 187 g of ethylenediaminetetraacetic acid were added. The growth was ended after 130 hrs. The extraction was carried out as in Example 1. The obtained crude extract contained, beside 3,200 g n-Paraffin S, which was recycled, 84.85 g of trehalosemycolate or 40%, based on the total trehalose lipids, and 78.28 g of trehalose tetraester or 60%, based on the total trehalose lipids.

EXAMPLE 4

Nitrogen Limitation

A 100 l bioreactor, provided with an intensor system, was charged with 50 l of nutrient salt solution (composition: 50 g yeast extract, 62 g citric acid $\times 1 H_2O$, 235.5 g $(NH_4)_2SO_4$, 25 g $KH_2PO_4$, 25 g $Na_2HPO_4 \times 2 H_2O$, 50 g 85% $H_3PO_4$, 2.5 g $CaCl_2 \times 2H_2O$, 1 g $FeCl_3 \times 6 H_2O$, 10 g $FeSO_4 \times 7 H_2O$, 55 g $MgSO_4 \times 7 H_2O$ and 50 l tap water, sterilized at pH 3.0 and at a temperature of 121° C. for 30 min.

After cooling to a temperature of 30° C., 4,900 g n-paraffin S (89% C-14, 9% C-15) were added, the pH adjusted to 5.8 with 10% NaOH solution and the mixture inoculated with 3,000 ml of a 24 hr.-old submerged culture of *Rhodococcus erythropolis* DSM 42 215. During the cultivation the submerged culture was automatically maintained at a constant pH of 5.8 by titration with a 10% NaOH solution, and aerated at a temperature of 30° C., an agitation rate of 2,000 rpm and an aeration rate of 1.5 V/V/m at a constant reactor pressure of 2 bars. The cultivation was ended after 140 hours. The extraction was carried out as in Example 1. The resultant crude organic extract contained, in addition to 3,300 g n-paraffin S, which was recycled, 37.9 g of trehalose mycolate or 10% based on the total trehalose lipids and 209.6 g of trehalose tetraester or 90% based on the total trehalose lipids.

EXAMPLE 5

Nitrogen Limitation and Temperature Shift

*Rhodococcus erythropolis* DSM 43 215 was cultivated as in Example 4 except that after 45 hrs. reaction time at 30° C. the temperature was lowered to 21° C. within 20 min. and the submerged culture continued for another 85 hrs. at this temperature. The resultant crude organic extract contained 3,500 g n-Paraffin S, which can be recycled, 59.8 g of trehalose mycolate or 10% based on the total trehalose lipids, and 330.9 g of trehalosetetraester or 90% based on the total trehalose lipids.

EXAMPLE 6

Nitrogen Limitation, Temperature Shift and Ethambutol Addition

*Rhodococcus erythropolis* DSM 43 215 was cultured as in Example 4, except that after sterilization of the nutrient salt solution, 0.75 g of aseptic Ethambutol (d-N,N'-bis (1-hydroxymethyl-propyl)-ethylenediamine dihydrochloride) was added and the cultivation temperature of 30° C. after 70 hrs. reaction time was lowered to a temperature of 21° C. within 20 min. The reaction was continued for another 115 hrs. at this temperature. The extraction, carried out as in Example 1, produced an organic crude extract, which contained, in addition to 3,400 g n-Paraffin S, which can be recycled, 215.2 g of trehalose mycolate or 30% based on the total trehalose lipids, and 308.8 g of trehalose tetraester or 70%,based on the total trehalose lipids.

EXAMPLE 7

Esterification of the anionic tetraester with diazomethane

The anionic tetraester (1.0 g) dissolved in dry ether was reacted at room temperature with exclusion of moisture, with a dry solution of diazomethane in diethyl ether until a yellow color persisted, or until further addition of diazomethane produced no more nitrogen evolution. Then the solvent was removed under vacuum. The reaction took place almost quantitatively to form the corresponding methyl ester.

EXAMPLE 8

Preparation of $\alpha,\alpha'$-trehalose from trehalose lipids 200 mg of the combined trehalose lipids (from Example 5) were dissolved in 10 ml ether and reacted with 20 ml of a 0.5M ethanolic solution (90%) of NaOH and heated for 12 hrs. under reflux. Then the reaction mixture was treated with 20 ml water and freed from the solvent under reduced pressure, acidified with dilute hydrochloric acid and the aqueous phase extracted three times with 20 ml diethyl ether. The aqueous phase was then freed from salts with ion exchange resins Amberlite IRA-400, H0-form and then Amberlite IR-120, H+-form and the aqueous solution freeze-dried. The yield of $\alpha,\alpha'$-trehalose amounted to 70 mg or 90% of theory.

EXAMPLE 9

Nitrogen Limitation

*Arthrobacter* spec. DSM 2567 was cultivated at 100 rpm and 30° C. in seven 500 ml Erlenmeyer flasks with baffle plates, each of which contained 100 ml of a preculture medium (composition: 30 g saccharose, 10 g meat extract, 10 g peptone, 3 g NaCl and 1 liter distilled water; pH 7 before sterilization). After 72 hours incubation, this culture suspension was transferred to a 10 l bioreactor provided with a flat blade paddle agitator, and was sterilized with 7 l of the following nutrient solution for 30 min. at 121° C.: 11.5 g steeped corn water, 16.9 g citric acid $\times 1H_2O$, 35 g $(NH_4)_2SO_4$, 25.8 g $KH_2PO_4$, 10 g $Na_2HPO_4 \times 2H_2O$, 7 g 85% $H_3PO_4$, 10.7 g $MgSO_4 \times 7H_2O$, 0.28 g KCL, 3 g $CaCl_2 \times 2H_2O$, 1.75 g $FeCl_3 \times 6H_2O$ and 7 l deionized water; pH 3.0. After cooling to a temperature of 30° C., 540 g of sterile n-Paraffin S (89% C-14, 9% C-15) was added to this medium before inoculation and the pH adjusted to 6.2 with 10% NaOH solution.

During the cultivation the submerged culture was automatically maintained at a pH of 6.2 with a pH controller by titration with a 10% NaOH solution and aerated with air at a temperature of 30° C., 350 rpm and an aeration rate of 0.8 V/V/m. After 144 hours, the culture suspension was extracted twice with 14 l of a $CH_2Cl_2/CH_3OH$ 2:1 solvent mixture and after concentration of the organic phase, 595 g of residue was obtained. This crude extract was dissolved in 2 l $CHCl_3$ and then agitated with 1 kg silica gel 60 for 30 min. Then it was filtered and the remaining silica gel washed twice with 2 l $CHCl_3$. After purification of the $CHCl_3$ solution and removal of the solvent under vacuum, there remained 270 g n-Paraffin S which could be recycled. The silica gel was stirred twice with 2 l $CH_3OH$ and after filtration the purified organic extract was concentrated. The residue contained 8.3 g of trehalose mycolate or 10% based on the total trehalose lipids, and 74.8 g of trehalose tetraester or 90% based on the total trehalose lipids.

EXAMPLE 10

Nitrogen Limitation

The growth of *Corynebacterium* spec. DSM 2568 was carried out at 100 rpm and a pH of 6.5 in ten 500 ml Erlenmeyer flasks with baffle plates, each of the flasks containing 100 ml of a culture suspension (composition: 0.2 g $Na_2HPO_4 \times 2H_2O$, 0.05 g $FeSO_4 \times 7H_2O$, 0.3 g steeped corn water, 0.2 g $KH_2PO_4$, 0.5 g $(NH_4)_2SO_4$, 0.002 g $MnSO_4 \times 1H_2O$, 0.1 g $MgSO_4 \times 7H_2O$, 0.01 g $CaCl_2 \times 2H_2O$, 0.001 g $ZnSO_4 \times 7H_2O$ and 100 ml of distilled water), which had been sterilized for 20 min. at a temperature of 121° C. After cooling to a temperature of 30° C., 10 g of sterile n-Paraffin S (89% C-14, 9% C-15) were added. Each 100 ml of culture were then inoculated with 2 ml of a 72 hr. old preculture (medium as described in Ex. 9) of *Corynebacterium* spec. DSM 2568.

During the cultivation, the pH value of the submerged culture was corrected daily to a pH of 6.5 with sterile 1 N NaOH solution. After 12 days incubation, an extraction of the purified reaction mixture with two 2 l portions of the solvent mixture $CH_2Cl_2/CH_3OH$ 2:1 produced, after evaporation of the solvent, 70 g of residue which was chromatographed in a glass column packed with silica gel 60 ($d_i$=4.5 cm, packed 40 cm high). Using $CHCl_3$ as eluting agent, there were obtained 65 g n-Paraffin S, which could be recycled. Elution with a $CHCl_3/CH_3OH$ mixture in the volume ratio of 5:1 to 1:2 yielded 0.3 g of trehalose mycolate or 10% based on the total trehalose lipids, as well as 2.6 g of trehalose tetraester or 90% based on the total trehalose lipids.

We claim:

1. A process for increasing the yield of trehalose lipids comprising the steps of cultivating a trehalose lipid-producing microorganism capable of utilizing n-alkanes aerobically in a sterilized aqueous culture suspension with a nutrient medium containing hydrocarbons at a temperature range of from 15° C. to 50° C., under limited growth conditions by maintaining the pH between 3 and 8 by addition of a nitrogen-free alkaline compound, stirring 10 to 20 g/l portions of an organic solvent selected from the group consisting of kerosene and a mixture of about 89 vol. % of $C_{14}$ and about 9 vol. % of $C_{15}$ n-paraffins into the culture suspension over the period of time during which logarithmic growth takes place at intervals of 14 to 59 hours which will not arrest the growth of said microorganism, lowering the temperature at the end of the logarithmic growth period and isolating the resulting mixture of trehalose lipids from the culture suspension.

2. The process according to claim 1, wherein the microorganism is *Rhodococcus erythropolis* DSM 43215, Arthrobacter DSM 2567 of Corynebacterium DSM 2568.

3. The process according to claim 1, wherein the culture suspension comprises at least 0.01 to 0.02 g/l of d-N,N'-bis(1-hydroxymethylpropyl)ethylenediamine dihydrochloride.

4. The process of claim 1, wherein the temperature is lowered to 21° C. at the end of the logarithmic growth period.

5. The process of claim 1, wherein the mixture of trehalose lipids is separated into non-ionic and anionic trehalose lipids.

6. The process of claim 1, wherein a pH range of between 5.8 and 6.5 is maintained.

* * * * *